United States Patent [19]

Bedding

[11] 4,334,498
[45] Jun. 15, 1982

[54] ASSEMBLAGE FOR REARING NEMATODES

[75] Inventor: Robyn A. Bedding, Taroona, Australia

[73] Assignee: Commonwealth Scientific and Industrial Research, Campbell, Australia

[21] Appl. No.: 251,435

[22] Filed: Apr. 6, 1981

Related U.S. Application Data

[63] Continuation of Ser. No. 57,151, Jul. 12, 1979, abandoned, which is a continuation-in-part of Ser. No. 909,404, Feb. 21, 1978, which is a continuation of Ser. No. 715,590, Aug. 18, 1976, abandoned.

[30] Foreign Application Priority Data

Aug. 26, 1975 [AU] Australia ............................. PC2930

[51] Int. Cl.³ ............................................. A01K 67/00
[52] U.S. Cl. ............................................. 119/1; 119/15
[58] Field of Search ................................. 119/1, 15, 6

[56] References Cited

U.S. PATENT DOCUMENTS

| 2,527,214 | 10/1950 | Graves | 119/1 |
| 3,465,720 | 9/1969 | Miyazawa et al. | 119/6 |
| 3,961,603 | 6/1976 | Gaddie, Sr. | 119/15 |
| 4,192,254 | 3/1980 | Apel | 119/1 |

Primary Examiner—Hugh R. Chamblee
Attorney, Agent, or Firm—Sughrue, Mion, Zinn, Macpeak and Seas

[57] ABSTRACT

An assemblage for rearing nematodes comprises a growth medium suitable for the culture of the nematodes, the growth medium being dispersed to allow free movement of fluids over the surface of the medium and to maximize the ratio of the surface area of the medium to volume of the assemblage. The assemblage may comprise an animal tissue homogenate as growth medium dispersed over the surface of elements of inert material such as wood-wool or crumbed plastics foam.

6 Claims, 1 Drawing Figure

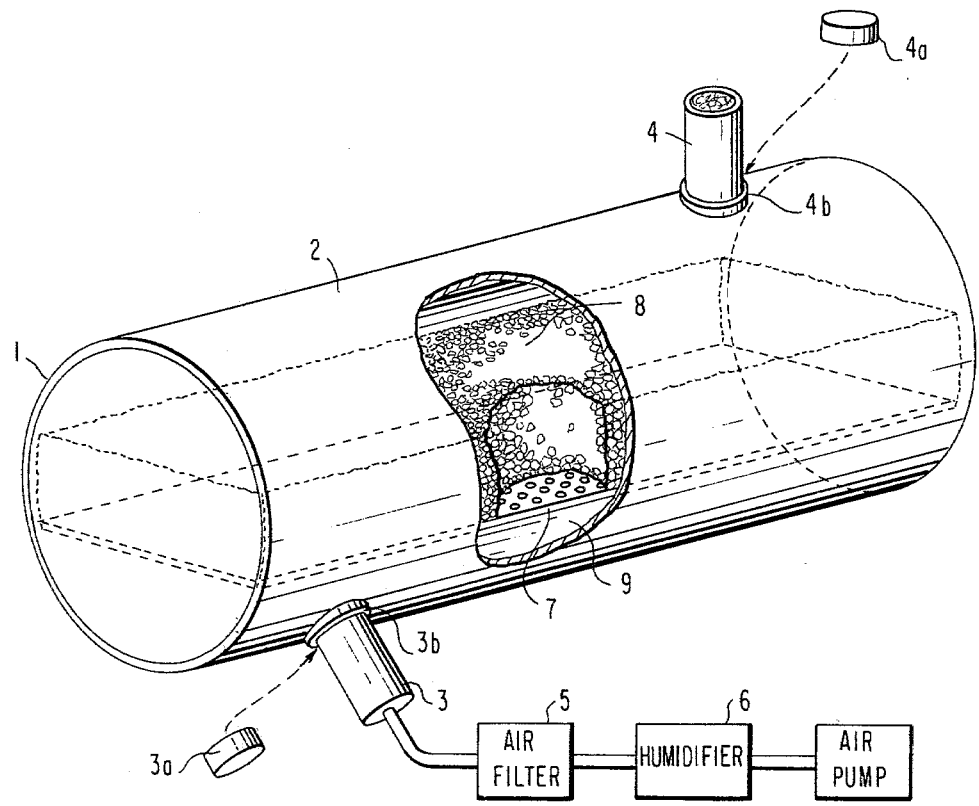

ASSEMBLAGE FOR REARING NEMATODES

CROSS-REFERENCE TO RELATED APPLICATIONS

The present application is a continuation of application Ser. No. 057,151 filed July 12, 1979, now abandoned which is a continuation-in-part of application Ser. No. 909,404 filed Feb. 21, 1978, which was a continuation of application Ser. No. 715,590, filed Aug. 18, 1976, now abandoned.

BACKGROUND OF THE INVENTION

This invention relates to the use of nematodes for biological control of insect pests.

The infective larvae of *Neoaplactana carpocapsae* have been observed to destroy a wide range of insect pests under laboratory conditions. This ability is accounted for by the nematode's own pathogenicity towards the insects, and by its association with the symbiotic bacterium, *Achromobacter nematophilus*, which is usually to be found in the intestinal lumen of infective species. Following ingestion by an insect, the nematode will usually penetrate the gut wall to enter the haemocoel and release *A. nematophilus* which mutliply and lead to the death of the host by septicaemia. Additionally, there will often be reproduction of the nematodes in the dead host and hence generation of further infective organisms.

In the light of the above, many proposals for the use of infective larvae of *N. carpocapsae* in the biocontrol of insects, have been published since the nematodes were first investigated. A major obstacle to the implementation of such proposals has, however, been the susceptibility of nematodes to desiccation. Their apparent need for free water has led to suggestions that they be applied via aqueous media to bark or foliage on which the insect pests feed, but only limited effectiveness has been achieved with this technique under field conditions because of evaporation of the water before the nematodes locate and become established in the host. In order to reduce the rate of evaporation, it has been advocated that aqueous formulations should include, for example, wax evaporation-retardants, water thickeners, and gelling agents or surfactants, Unfortunately there is little evidence that such formulations so extend the life-time of nematodes in the field after application that they can be regarded as offering an effective and practical method of insect control.

It has been discovered that infective nematodes will remain active for substantial periods of time in the absence of free water, provided their body moisture, oxygen supply and mobility can be maintained, and that this can be achieved by use of oil instead of water as a medium in which to store or disperse the nematodes.

Many natural and synthetic oils possess appropriate oxygen permeability (i.e. high, relative to water), ability to reduce loss of body moisture, and mobility, to render them useful for this purpose, but some care is obviously necessary to avoid materials which although satisfactory in terms of physical properties, are toxic to the parasites. Optimum physical properties will vary according to factors such as the mode of application of the oil suspension and the conditions prevailing at the time of application. For most purposes a light mineral oil is recommended, and preferably a paraffinic oil containing no additives; we have found mineral oils with S.A.E. viscosity ratings in the range of about 50–250 to be satisfactory. One commercial example is DENTAX 140 oil produced by the Shell Company, another is TALPA 60, also produced by the Shell Company.

A preferred feature of such formulations is the addition of waxes and wax-like materials to the oil, to assist in reducing moisture loss from the nematodes. The beneficial effect of the wax is believed to derive from its tendency to migrate to the exterior of the oil droplet and form a coating which is substantially impermeable to water but not to oxygen. The wax is selected so as to have a melting point above the ambient temperature likely to be encountered during storage or in the field, but preferably it should be possible to mix it with the oil while molten in order to facilitate dispersion. Paraffin waxes with melting points of the order of 115–145° F. are suitable when included in amounts from about 5 to 15% (by weight of oil). Although nematode survival (after spraying onto plants) is favoured by wax concentrations at the upper end of this range, a better kill is achieved with compositions containing less wax, about 6–8%, appears to be optimum; the latter compositions are also easier to spray. Although generally inferior to paraffin wax, acceptable alternatives include vaseline, petroleum jelly, wool wax, wool grease, microcrystalline wax and match wax.

A typical effective nematode medium has the following composition:

5–15 parts 135/145 paraffin wax

95–85 parts TALPA 60 oil.

In addition, satisfactory performance is achieved when DENTAX 140 or TALPA 50 oils are used instead of TALPA 60, or 115/125 and 125/135 paraffin waxes are substituted in part or whole, for 135/145 paraffin wax.

It is difficult to say with precision how much oil medium is required to sustain a given number of nematodes; good results have been achieved with as many as 500,000/ml, but generally it is preferred to work with concentrations of the order of 200,000/ml.

When applied in an oil/wax formulation such as described above, the loss of moisture is so retarded that the nematodes take several hours to several days to desiccate, and even then they may be revived by moistening, as will occur upon ingestion by an insect. By contrast, nematodes subjected to the rapid drying, which is a feature of techniques employing aqueous formulations, die within a few minutes of the free water being lost.

Another discouragement to the use of nematodes as biological control agents for insects has hitherto arisen when attempts have been made to produce nematodes in quantity. Although small batches can be reared quite successfully in small vessels, such as petri dishes, containing growth media, when larger vessels are used the output is not found to be commensurate with the increased scale of operations. It is believed that this is because large uninterrupted masses of growth media are more easily contaminated by foreign bacteria, and also there are difficulties in aerating and harvesting nematodes from such masses of growth media. Such problems are minimised in a new method provided by the present invention.

SUMMARY OF THE INVENTION

According to this invention there is provided an assemblage for rearing nematodes comprising a growth medium suitable for the culture of the nematodes, said growth medium being dispersed to allow free movement of fluids over the surface of said medium and to maximise the ratio of surface area of said medium to volume of said assemblage.

This invention also provides a method of rearing nematodes which comprises introducing nematode larvae to an assemblage as described above.

In general, the invention provides for the rearing of nematodes in an assemblage of suitable sterilised growth medium which is liberally provided with interconnected interstitial spaces to permit the free circulation of fluids, namely air for aeration and washing liquids for harvesting.

The assemblage and method of this invention are particularly suited to the rearing both of Neoaplectana species to which insect species from a variety of orders have proved susceptible, and of Heterorhabditis species which appear to be equally nonhost specific and may be even more virulent against various soil-dwelling insects than are Neoaplectana species.

BRIEF DESCRIPTION OF THE DRAWING

The single FIGURE discloses a schematic view, partly in section of one form of apparatus for carrying out the present invention.

DETAILED DESCRIPTION OF THE INVENTION

The apparatus as shown in the drawing is comprised of a stainless steel drum 2 having a lid 1 sealed by a rubber gasket. A stainless steel apertured shelf 7 is supported within the drum parallel to but offset from the equator and separates a support medium 8 from an underlying air/drainage space 9. A stainless steel tube 4 lightly packed with absorbent cotton wadding is screwed into an upper hole 4b. The tube 4 can be replaced by an airtight stopper 4a. Similarly, a tube 3 can be screwed into the lower hole 3b and is connected in series to an air filter 5, an air humidfying means 6 and an air pump. During sterilizing the tube 3 can be replaced by the airtight stopper 3a.

An effective mass-rearing assemblage may be formed in accordance with this invention in a variety of ways, for example by loosely stacking animal organs or pieces of animal organs, or pieces of animal tissue, or pieces of inert material coated or impregnated with an animal tissue homogenate. (Animal in this discussion is intended to include avian). Small stacks may be self-supporting, but above a certain size, depending on the material being used and proportions of individual components, it may be necessary to provide supports in the form of spaced trays or grids made from plastic, stainless steel, wood or other inert material. Instead of trays or grids, assemblages of cellular or coiled material may be employed, for instance as layers interposed between layers of the pieces of the growth medium, or as a substantially continuous network impregnated with a growth medium such as an animal tissue homogenate.

The output of a given assemblage will be related to the surface area of the growth medium it presents. Whilst a stack of pieces of animal material is relatively simple to construct and should remain coherent through repeated harvesting cycles without undergoing compaction or disintegration, it will be relatively inefficient from the point of view of surface area/volume ratio. It has been found that a stack with high surface area/volume ratio and correspondingly better initial output, may be made from a material such as wood-wool, especially Aspen wood-wool, coated with a suitable growth medium such as animal tissue or homogenate. Among other materials useful for increasing the surface area of a stack are wood shavings, straw, coke, choppings of plastic tubing, or sections of folded aluminium sheet. A particularly effective material which provides a large surface area in three dimensions with adequate interstitial space for migration and aeration consists of "crumbed" or broken-up plastics foam or sponge, such as polyether polyurethane foam (which is widely used commercially and waste off-cuts of which are "crumbed" for use as pillow or cushion filling), the bulk of which may, for example, consist of pieces varying in size from about 1 cm$^3$ to 10 cm$^3$. The actual density of this material appears to have little effect on its utility in the present invention, except that the coarsest material tends to collapse when growth medium is applied thereto and the finer material tends to become clogged up. A thin coating of growth medium such as animal tissue homogenate may be applied throughout such a material.

Particularly effective growth media for the mass culture of nematodes in accordance with this invention have been found to be:

I

70% Pigs kidney
10% Fat
20% Tap Water

II

60% Pigs kidney
20% Fat
20% Tap Water

Other homogenate formulations which have been shown to be effective growth media for rearing of nematodes in accordance with this invention include:

III 3 parts chicken heart
3 parts pig kidney
2 parts water
0.05% cholesterol.

IV 3 parts chicken heart
2 parts water

V 3 parts chicken heart
1 part chicken liver
2 parts water

VI 1 part soy bean
4 parts water

VII 2 parts beef heart
1 part water

A typical sequence of operations in rearing nematodes in accordance with this invention would be: (i) adding inoculae of nematodes and symbiotic bacteria to a sterilised assemblage, which is maintained in a moist, aerated condition; (ii) after a period allowing for suitable multiplication, harvesting the nematodes by washing with sterile water; if desired, (iii) filtering the nematodes from the wash water; and if desired, (iv) mixing the nematode filter cake with oil or oil and wax to produce compositions for storage or application.

The oil or oil and wax compositions prepared as described above can be stored for several days if maintained at about 0–10° C. in sealed containers which have been flushed with oxygen. When the nematodes are to be applied in the field, the composition is removed from storage, allowed to reach ambient temperature, and then applied to the foliage of the affected plant through high pressure sprays which form a mist of the formulation in which droplets contain one or at most a few nematodes. Suitable spraying apparatus for small scale work is a paint spray gun, using compressed air at about 15 lbs. per square inch pressure.

For long term storage, it is known that high concentrations of nematodes can be kept alive suspended in water through which air is bubbled at a rate sufficient to ensure that all nematodes are subject to some degree of agitation. For example, it has been found possible to keep as many as $10^9$ nematodes alive for several weeks in 2 liters of water at 5° C., using a $2\frac{1}{4}$ liter flagon supported with the base at 45° to the horizontal and with air being introduced from an aquarium pump through a tube reaching into the lower corner. Under the same conditions, lesser concentrations have been kept alive for over a year. It is a simple matter to connect several containers in series to the same pump.

Having broadly portrayed the nature of the present invention, particular examples will now be described by way of illustration only.

EXAMPLE 1

In this particular example the nematode *Neoaplectana carpocapsae* strain Agriotos was employed. The nematodes were reared in monoxenic culture together with their symbiotic bacterium *A. nematophilus* to produce an inoculum of approximately one million individuals by small-scale batch culture. A media stack was formed from whole chicken hearts arranged in alternating layers with wood shavings and supported at intervals by wire mesh trays arranged vertically one above the other, within a sealable drum having inlets and outlets for sterile air at either end. The interior of the drum and its entire contents were then subjected to heat-sterilisation by passing steam therethrough. The inoculae of bacteria and nematodes were mixed with sterile distilled water and simply poured into the sterile drum to disperse the microorganisms over the layers of media. The drum was then incubated at about 25° C. for about 3 weeks to allow infective nematodes to be produced. These nematodes migrated to the surface to the chicken hearts and onto the wood shavings from whence they could be readily harvested by flushing with sterile water. Sufficient nematodes and bacteria were, however, left within the drum to produce a second generation which were incubated and harvested in the same manner. In this way repeated harvestings could be effected as the chicken hearts and wood shavings stack does not compact, the chicken hearts merely shrinking in size but retaining their coherence and individuality.

The nematodes were separated from the wash water after harvesting by decanting surplus water and then filtering through a spinning screen, or other filter membrane such as Whatman's No. 1 filter paper, to produce a filter cake. Excess water was then removed from the filter cake by allowing it to stand for a short period and by dabbing with absorbent material. A concentrate of nematodes was then formed by vigorous mixing with about 10 times its own volume of a grease-like material produced by heating 8% Shell 140/145 paraffin wax and 92% Shell TALPA 60 in a water bath, and then allowing the mixture to cool to about 10° C.

EXAMPLE 2

A mixture of four parts chicken hearts to three parts water was homogenised for about three minutes in a household food blender. The homogenate was mixed by hand with dry, course grade Aspen woodwool; the wool being squeezed and teased so that each strand was discrete but well coated with an even layer of the homogenate. The coated woodwool was then put into 2 liter Pyrex glass aspirators (giving about 320 g homogenate per aspirator); the mouth of each of these was closed with non-absorbent cotton wool bungs and the bottom inlet attached to an air filter tube prior to autoclaving for 1 hour. Monoxenic inoculum of about 1 million Neoaplectana was added through the mouth of each aspirator and air at 100% relative humidity was blown through the filter tube, entering the bottom of the aspirator and leaving at the top. The aspirator and contents were incubated at 23° C. for three weeks. A first harvesting (with sterile salt solution) yielded over $5 \times 10^7$ infective nematodes, and a similar yield was harvested after a further 3 weeks.

EXAMPLE 3

Culture flasks are prepared in which an animal tissue homogenate growth medium is supported on crumbed plastics foam in the amount of 12 parts homogenate to 1 part of crumbed foam. A homogenate of 70% pigs kidney, 10% fat and 20% tap water is used for Neoaplectana species and one of 60% pigs kidney, 10% fat and 20% tap water for Heterorhabditis species.

The kidneys are blended with 20% water and thoroughly homogenised before the required amount of lard is added (melted and heated to just below boiling point) and thoroughly blended into the kidney/water mix. The resulting homogenate is added to the crumbed foam in a container and thoroughly and evenly distributed by stirring and squeezing the foam. The coated foam is then loaded by funnel to two-thirds fill 500 ml Erlemeyer flasks, and the flask necks are thoroughly cleaned and closed with lightly rolled bungs of non-absorbent cotton wool. After covering the bungs with aluminium foil, the flasks are sterilised by autoclaving for 3 hours. After autoclaving, and preferably while still warm, the clumped pieces of foam are broken up by tapping or hitting the flasks repeatedly against one hand. When cold, the flasks are ready for inoculation but they may be stored for several weeks if required. Inoculation is initially accomplished by adding a monoxenic inoculum of the nematodes to be cultured and then symbiotic bacteria under sterile conditions to the sponge surface, but when flask cultures are established inoculation is more easily performed, and bigger yields are obtained, by shaking about 1/20 the contents of a mature flask culture into the flask.

When the inoculum is added in this way without prior introduction of the primary form of the symbiotic bacterium to the flask, results may be initially good if variable, but after continual subculturing yields tend to decline. Thus, for optimal and consistent yields, it is better to inoculate the flask first with a liquid culture of primary form bacteria; this may be prepared by adding a selected colony of the primary form bacteria from a plate to MacCartney bottles half filled with Yeast extract broth or normal nutrient broth, and shaking the bottles at 20°-30° C. for 1 to 2 days. Using a sterile syringe, 10 mls of broth, or broth diluted with 1% salt solution, are gradually introduced into each flask while the flask is agitated so that the inoculum is distributed over as much of the growth medium coated foam as possible. The flasks are then shaken vigorously by hand to further distribute the bacteria, incubated at 20°-30° C. for one to two days and then inoculated with nematode culture. Optimal yields are obtained after 2 to 3 weeks with Neoaplectana and 3 to 4 weeks with Heterorhabditis at 20°-28° C. depending upon species and at 90° relative humidity.

While flask cultures are adequate for the production of hundreds of millions of nematodes, far larger numbers can be produced more efficiently using bigger containers. Examples 4(a) and (b) illustrate the use of two kinds of larger containers which require slightly different treatment procedures.

EXAMPLE 4

(a) Stainless steel cylinders 35 cm diameter and 12 cm deep with stainless steel bases and heavy duty disposable overlapping lids (at least 5 cm turned down against sides) made of aluminium foil are loaded with 2 Kg of growth medium on crumbed plastics foam or sponge (prepared as for culture flasks) autoclaved for 5 hours and inoculated soon after preparation and cooling.

For good results, these should be inoculated firstly with primary form symbiotic bacteria and after 2-3 days with nematodes. Bacterial inoculation is accomplished using 200 mls of diluted suspension which is best squirted over the sponge, using a sterilised repipette, while the sponge is raked and broken up with a long sterile wire hook. The sponge is then thoroughly raked and mixed to maximise bacterial distribution and incubated at 22° C. for two days; the total contents of one culture flask of nematode culture is scattered over the surface and the container incubated at 20°-28° C. 90% relative humidity. Since incubation is rather prolonged all inoculation procedures are best performed in a laminar flow cabinet after prior surface sterilisation of the container (conveniently accomplished by thoroughly spraying with 70% alcohol).

(b) The second type of containers which may be loaded with up to 10 Kg of medium are 60 liter 35 cm diameter stainless steel drums with lids sealed by rubber gasket. Inside each drum is a stainless steel 0.5 cm mesh shelf which runs along the drum parallel to and about 8 cm from the equator and separates the medium from an underlying air/drainage space when the drum is laid horizontally. At one end of the drum, lying at right angles to the shelf is a 5 cm hole threaded to take an air tight stopper; this is used for bacterial and nematode inoculation and later as an air outlet. At the other end on the underside of the shelf but offset so it lies only 2 cm from the shelf is a similar hole 2.5 cm diameter also with an air tight stopper; this is a drainage hole and air inlet.

The drums are each loaded with 10 Kg of growth medium coated sponge and autoclaved for about ½ hour to pre cook the medium and the sponge is then thoroughly broken up prior to a further 6 hours autoclaving with the lid sealed and with light non-absorbent cotton wool plugs in the inlet and outlet holes. The cotton wool plugs are replaced by air tight stoppers after autoclaving and the drum rolled and agitated to break up and loosen the sponge before inoculating when the drum is cool with 1000 ml suspension of primary form bacteria. Further rolling and agitation of the drum just after and at one and two days after inoculation ensures thorough distribution of primary form bacteria throughout the medium. Between the second and third day the drum is left in a horizontal position with the mesh shelf beneath the medium. Inoculation with nematodes is made three days after inoculation with bacteria; surplus liquid is first drained from the drainage hole and then the contents of 3 mature culture flasks of nematodes are introduced into the inoculation hole with some agitation of the drum to give partial separation of the inoculum. With both plugs sealed, the drum is now tipped end to end two or three times and shaken a little so as to distribute inoculum, but without spreading secondary form bacteria (which inevitably occurs on mature inoculum) all over the fresh medium. The drum is now placed so that the inner shelf is horizontal and the medium is lightly agitated to evenly cover the shelf. An air outlet consisting of a 10 cm long, threaded stainless steel tube lightly packed with the absorbent cotton wool is screwed into the upper hole; an air inlet tube 5 cm long is screwed into the lower hole and connected to the air moistening, air filtering and air pump units. The drum is then incubated at 22 to 28° C. depending on nematode species and harvested after 3 to 4 weeks.

It will be noted that in Examples 3, 4(a) and 4(b) above, the growth medium is incubated with cultures of primary form symbiotic bacteria. It has been found that the understanding of the dimorphic status of these bacteria is of importance in that whilst nematode reproduction is optimal on the primary form, it is greatly reduced when abundant secondary form is present. Only the primary form of the symbiotic bacteria is usually found in mature infective nematodes, such as species of Neoaplectana and Heterorhabditis, and when this is released into the haemocoel of the insect it maintains its purity (from the secondary form) or at least dominates, for the first few days; later the secondary form is produced within the cadaver and this also occurs on artificial media. With all symbiotic bacterial isolates, the primary form is more mucoid, the colonies are more domed and more opaque and, where pigmentation occurs, the pigmentation is more pronounced. Colonies of primary form *A. nematophilus* readily absorb bromothymol blue dye in contrast to colonies of the secondary form.

A pure culture of the primary form of the symbiotic bacteria derived from the strain of nematodes to be cultured may, for example, be obtained by firstly placing surface sterilised infective nematodes in hanging drops of insect blood or by crushing surface sterilised infective stages in a tissue homogeniser. Suitable colonies of primay form bacteria are selected after streaking out on plates of nutrient agar and added to sterile salt solution which is used for inoculation.

The primary form of the symbiont bacteria is maintained in culture, but with some difficulty, in Y.S. broth; sub cultures are made fortnightly and incubated at 12° C. and tested regularly to ensure absence of the secondary mutant. For maintenance of pure primary form over long periods, ampules of freeze dried primary form are prepared from bacteria recently isolated from mature infective stages.

Basic monoxenic cultures of nematodes particularly suited for use in the mass culture methods of Examples 3, 4(a) and 4(b) may be established and maintained on animal tissue homogenate (90% pig kidney, 10% beef lard) on nutrient agar slopes in test tubes by the following procedure:

1. Add 0.5 ccs of a pure suspension of symbiotic bacteria, derived from the strain of nematodes to be established, to a tube slope so that it spreads over the agar and kidney medium; this is incubated at 20°–30° C. for two days.

2. Select unsheathed infective stage larvae that are at least two weeks old and wash thoroughly in tap water by sedimentation in syracuse watchglass or by centrifuging; then divide into batches of fifty in watch glasses and examine using a dissecting microscope; all dead and non infective stages must be removed.

3. Pipette out water and replace with 0.1% merthiolate solution; after about 1 hour transfer each suspension of nematodes into fresh 0.1% merthiolate, solution in sterile syracuse watch glasses in a sterile base and leave for 3 hours; wash three times in sterile tap water using a sterile pipette.

4. Add each batch of 50 now surface sterilised infective stages, in a minimum of water, to the culture tubes previously infected with symbiont, and incubate at 20°–28° C. (depending on climate of locality from which nematodes were originally obtained).

5. When reproduction within tubes has largely ceased and abundant infective stages are present (usually after about 1 month) sub cultures may be made onto fresh slopes and while vigour is maintained it is not necessary to first add primary form symbiont bacteria.

It is also to be understood that pest control technology is not the only field of application for the methods of quantity production of nematodes which are described herein. For instance live nematodes are very acceptable as food to many species of fish, and nematode cultures are commercially available for tropical fish enthusiasts to generate live food for their aquaria. It is envisaged that there would be a similar market for live adult nematodes produced by the method of this invention, particularly if packaged in watertight, airpermeable containers which were also suitable for refrigerated storage.

References in this specification to "parts" or percentages when describing growth media or oil media, are to be understood as meaning parts or percentages by weight.

The claims defining the invention are as follows:

1. A method for rearing nematodes comprising introducing a growth medium into a sealable container having a suitable support medium therein, sterilizing the contents of said container, inoculating said growth medium with a symbiotic bacteria for said nematodes, inoculating said growth medium with a nematode culture and incubating said nematode culture in said container.

2. A method for rearing nematodes as set forth in claim 1, comprising deriving said symbiotic bacteria from the strain of nematodes to be cultured.

3. A method for rearing nematodes as set forth in claim 1, wherein said incubating is carried out by maintaining the inoculated growth medium in a moist aerated condition for a sufficient period of time to allow for multiplication of said nematodes.

4. A method for rearing nematodes as set forth in claim 1, further comprising the steps of harvesting said nematodes by washing said growth medium with sterile water or salt solution and filtering the harvested nematodes from the wash solution.

5. A method for rearing nematodes as set forth in claim 1, wherein said support medium is comprised of crumbed or broken up plastics, foam or sponge.

6. A method for rearing nematodes as set forth in claim 1, wherein said growth medium is comprised of an homogenate dispersed over the surface of said support medium.

* * * * *